United States Patent [19]
Kyle et al.

[11] Patent Number: 5,749,872
[45] Date of Patent: May 12, 1998

[54] KEYED/KEYLESS BARREL FOR BONE PLATES

[75] Inventors: Richard F. Kyle, Long Lake, Minn.; Richard H. Clewett, Los Angeles; Drew D. Wright, Santa Monica, both of Calif.

[73] Assignee: Ace Medical Company, El Segundo, Calif.

[21] Appl. No.: 525,853

[22] Filed: Sep. 8, 1995

[51] Int. Cl.$^6$ .................................................. A61B 17/58
[52] U.S. Cl. .................. 606/69; 606/70; 606/65; 606/66; 606/73
[58] Field of Search ............................ 606/65–73

[56] References Cited

U.S. PATENT DOCUMENTS

| | | |
|---|---|---|
| 2,702,543 | 2/1955 | Pugh et al. . |
| 2,834,342 | 5/1958 | Yost . |
| 3,094,120 | 6/1963 | Blosser . |
| 3,103,926 | 9/1963 | Cochran et al. . |
| 3,374,786 | 3/1968 | Callender, Jr. . |
| 3,842,825 | 10/1974 | Wagner ........................ 128/92 B |
| 4,095,591 | 6/1978 | Graham, Jr. et al. ............ 128/92 |
| 4,172,452 | 10/1979 | Forte et al. .................... 128/92 |
| 4,432,358 | 2/1984 | Fixel ........................... 128/92 |
| 4,530,355 | 7/1985 | Griggs .......................... 128/92 |
| 4,657,001 | 4/1987 | Fixel ........................... 128/92 |
| 4,759,352 | 7/1988 | Lozier .......................... 128/92 |
| 5,032,125 | 7/1991 | Durham et al. ................. 606/62 |
| 5,041,114 | 8/1991 | Chapman et al. ............... 606/69 |
| 5,176,681 | 1/1993 | Lawes et al. ................... 606/64 |
| 5,324,292 | 6/1994 | Meyers ......................... 606/66 |
| 5,364,398 | 11/1994 | Chapman et al. ............... 606/69 |
| 5,454,813 | 10/1995 | Lawes .......................... 606/62 |
| 5,458,601 | 10/1995 | Young, Jr. et al. .............. 606/72 |

OTHER PUBLICATIONS

Fracture Management, Versa–FX Femoral Fixation System, "Surgical Technique for Fixation of Supracondylar Fractures of the Femur", pp. 18–27.

Alta Modular Trauma System, "The Leading Edge in Fracture Management Technology ... Femoral Hip Fixation and Plate Module", Pfizer Hospital Products Group, Inc., 1989.

Clinical and Biomechanical Documentation of the Alta Modular Trauma System, "A Modular Titanium Femoral Fixation System", Michael W. Chapman, M.D. et al., pp. 1–12.

May Anatomical Bone Plate, "May Distal Femur Bone Plates", Link America, Inc., pp. 8–9.

European Compression Technique, Reference Manual, Zimmer USA, pp. 66–79.

DHS/DCS Dynamic Hip and Condylar Screw System, Technique Guide, Synthes.

Surgical Technique, "Richards Classic—Hip Screw and Supracondylar Plate, The Standard in Strength, Security and Stability", Smith + Newphew, pp. 1–18.

Fracture Management, Versa–FX Femoral Fixation System, "Surgical Technique for Fixation of Intertrochanteric Fractures of the Femur", pp. 4–14.

*Primary Examiner*—Michael Buiz
*Assistant Examiner*—Daphna Shai
*Attorney, Agent, or Firm*—Kinney & Lange

[57] ABSTRACT

A fixator for internally fixating bone fractures includes an elongate plate portion, a head portion and a barrel extending from the head portion. The elongate plate portion defines at least one plate aperture extending through the plate for receiving bone screws to fasten the fixator to a shaft of a bone. The barrel extends from the head portion and has a generally cylindrical inner surface configured for slidably receiving an end of both keyed and non-keyed lag screws. The cylindrical inner surface further defines at least one keyway along a length of the tube for receiving a key of a keyed lag screw to prevent rotation of the keyed lag screw and for also allowing rotation of a non-keyed lag screw.

9 Claims, 5 Drawing Sheets

KEYED/KEYLESS BARREL FOR BONE PLATES

BACKGROUND OF THE INVENTION

The present invention relates to internal bone fracture fixators. In particular, the present invention relates to a bone fracture fixator having a barrel configured for receiving both keyed and keyless lag screws.

The femur, otherwise known as the thigh bone, generally comprises an elongate shaft extending from the hip to the knee. The proximal end of the shaft includes a head, a neck, a greater trochanter and a lesser trochanter. The head of the femur fits into a concavity of the hip bone to form a ball and socket joint at the hip. The distal end of the femur includes a medial condyle and a femoral condyle. The condyles engage an upper end of the tibia to form the knee joint. Overall, the femur is the longest and strongest bone in the skeleton. However, portions of the femur are extremely susceptible to fracturing.

Fractures of the femur occur in both the proximal portion of the femur and the distal portion of the femur. Fractures of the proximal portion of the femur (hip fractures) are generally classified as femoral neck fractures, intertrochanteric fractures and subtrochanteric fractures. Fractures of the distal portion of the femur (knee fractures) are referred to as supracondylar fractures. Supracondylar fractures generally extend vertically between the condylars at the lower end of the femur to separate the distal portion of the femur into two main bone fragments. This fracture line may be further comminuted to create a plurality of smaller bone fragments.

Operational treatment of the fractures requires that the fractures be internally fixed and possibly compressed. Typically, the fractures are fixed and compressed with a lag screw inserted across the particular fracture line and supported by a plate mounted along the shaft of the bone or femur. When the proximal portion or the distal portion of the femur is fractured into two main bone fragments, a tube-plate fixator comprising a plate having a tube or barrel extending from a lower end of the plate is utilized to fix and compress the main bone fragments. The tube slidably receives an end of the lag screw. In such arrangements, the lag screw further includes a threaded interior for threadably receiving a compression screw. The compression screw is inserted through the tube and into the threaded bore of the lag screw so that rotation of the compression screw retracts the lag screw towards the plate to compress the two main bone fragments.

Although conventional tube-plate fixators provide rigid support for fixing and compressing the two main bone fragments caused by a vertical fracture line, conventional tube-plate fixators are not capable of fixing the plurality of additional smaller bone fragments created by comminuted fracture lines. Because tube-plate fixators support only one lag screw, the tube-plate fixator is capable of only fixing one main vertical fracture line. Furthermore, because the portion of the plate supporting the tube has a deminimus area, conventional tube-plate fixators lack sufficient buttressing area for adequately stabilizing the additional smaller bone fragments caused by comminuted fracture lines. In cases where the fracture lines are further comminuted to create a plurality of additional smaller bone fragments, fracture plates are used in lieu of conventional tube-plate fixators. Fracture plates mount to the femur and define a plurality of apertures at one end for supporting a plurality lag screws.

Typically, tube-plate fixators have one of two distinct barrel-lag screw configurations to fix and compress vertical fractures: keyless and keyed barrel-lag screw configurations. Keyless barrel-lag screw configurations utilize barrels with generally cylindrical inner surfaces and lag screws having corresponding cylindrical ends which are slidable and rotatable within the barrels. Because the lag screw is rotatable within the barrel, the barrel may be easily positioned over an end of the lag screw once the lag screw is screwed into the fractured bone. As a result, placement of the fixators is simplified.

Although simpler to implant, keyless barrel-lag screw configurations permit the lag screw and the coupled bone fragments to rotate with respect to the barrel. Once the lag screw is inserted across the vertical fracture line, the lag screw is subject to extreme forces which may cause the lag screw and its coupled bone fragments to rotate with respect to the barrel or tube of the plate. To prevent undesirable rotation of bone fragments, the lag screws and barrels are keyed to one another. The keyed configuration prevents rotation of the lag screw with respect to the barrel by forming a protuberance on the generally cylindrical inner surface of the barrel and by forming a corresponding detent on the cylindrical outer surface of the lag screw so that the end of the lag screw and the barrel mate in a non-rotatable relationship. For example, a keyed barrel-lag screw configuration may comprise a barrel having a rectangular inner surface and a lag screw having a rectangular outer surface to prevent rotation of the lag screw with respect to the barrel. Although keyed tube-lag screw configurations prevent rotation of the lag screw with respect to the barrel, placement of the plate and the barrel adjacent the femur and over the end of the lag screw is more difficult because the corresponding non-cylindrical shapes require the inner surface of the barrel and the outer surface of the lag screw to be in exact alignment for the end of the lag screw to be received within the barrel.

Present day keyless and keyed barrel-lag screw configurations have one severe drawback, lack of interchangeability. Because the barrel of a keyed barrel-lag screw configuration includes a protuberance or obtrusive portion projecting into the bore of the barrel for keying with a keyed lag screw, the keyed barrel of the fixator cannot receive the generally smooth cylindrical end of a keyless lag screw. Thus, separate fixators are required to accommodate keyed and keyless lag screws. As a result, separate inventories of relatively expensive, space consuming fixators for both configurations must be maintained.

SUMMARY OF THE INVENTION

The present invention is an improved system for internally fixing bone fractures. The system includes a fixator having a barrel with a cylindrical inner surface for rotatably and slidably receiving a cylindrical end of a keyless lag screw. The cylindrical inner surface further defines a keyway along at least a portion of the length of the barrel for allowing the barrel to slidably receive a keyed lag screw to prevent rotation of the keyed lag screw. As a result, the fixator of the present invention is usable with both keyed and non-keyed lag screws.

DETAILED DESCRIPTION OF THE PREFERRED EMBODIMENTS

Figure 1:
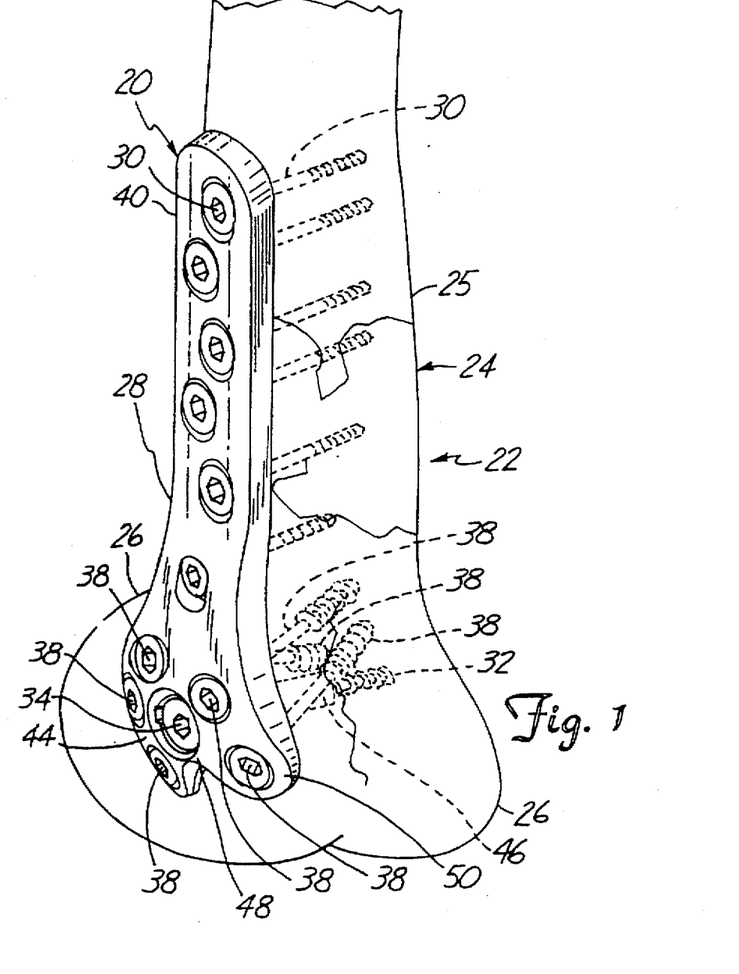
FIG. 1 is a perspective view of an internal fixating system mounted to a distal end of a femur.

FIG. 1 is a perspective view of an internal fixating system 20 implanted and mounted to distal end 22 of femur 24 having a shaft portion 25 and condyle 26. Fixating system 20 generally includes: fixator 28, bone screws 30, keyed lag screw 32, compression screw 34, and supplemental lag screws 38. Fixator 28 is mounted to femur 22 and generally includes plate portion 40, head 44 and tube or barrel 46. As best shown by FIG. 1, plate portion 40 is an elongated member coupled to head 44 and barrel 46. Plate portion 40 is mounted to femur 24 by bone screws 30. Fixator 28 is preferably formed from a titanium alloy. Alternatively, fixator 28 may be formed from any materials.

Head 44 extends from plate portion near condyles 26 of femur 22. Head 44 is generally circular in shape, somewhat in the shape of a baseball catcher's mitt and includes barrel portion 48 and support portion 50. Barrel portion 48 is generally the central portion of head 44 and supports barrel 46 and keyed lag screw 32. As can be appreciated, barrel portion 48 may alternatively be off set or eccentric.

Support portion 50 extends outward from barrel portion 48 and Generally away from plate portion 40. Support portion 50 supports and maintains supplemental lag screws 38. Supplemental lag screws 38 extend through support portion 50 and extend across comminuted fracture lines into smaller bone fragments. Supplemental lag screws 38 threadably engage bone fragments to pull the bone fragments toward support portion 50 of head 44. As a result, smaller bone fragments are also compressed and fixed by supplemental lag screws 38. Support portion 50 further provides a buttressing surface for abutting femur 24 adjacent condyles 26.

Barrel 46 is generally tubular in shape and extends from head 44 into femur 24. Preferably, barrel 46 does not extend across a vertical fracture line. Barrel 46 slidably receives keyed lag screw 32. Barrel 46 preferably has an inner diameter sized in close tolerance with an outer diameter of keyed lag screw 32 to prevent wobbling or inadvertent movement of keyed lag screw 32 within barrel 46. Barrel 46 rigidly supports keyed lag screw 32 with respect to fixator 28. As a result, barrel 46 provides additional strength to the compression and fixation of the main bone fragments separated by a vertical fracture line.

Keyed lag screw 32 includes a keyed end (not shown) slidably received within barrel 46 of fixator 28. Keyed lag screw 32 extends across a vertical fracture line and threadably engages main bone fragments separated by a vertical fracture line. Keyed lag screw 32 further includes a threaded inner bore (not shown in FIG. 1) partially extending into the keyed end and sized for threadably receiving compression screw 34. Keyed lag screw 32 is preferably formed from pure titanium or an alloy thereof. Alternatively, keyed lag screw 32 may be replaced with a keyless lag screw which includes a smooth cylindrical keyless end (not shown) slidably received within barrel 46 of fixator 28.

Compression screw 34 is conventionally known and extends through barrel 46. Compression screw 34 is threadably received within the threaded inner bore of keyed lag screw 32. Rotation of compression screw 34 causes the keyed end of keyed lag screw 32 to retract within barrel 46 towards head 44 and plate portion 40 of the fixator to compress main bone fragments of condyle 26 towards one another. Barrel 46 guides the retraction of lag screw 32 during compression of the bone fragments. Compression screw 34 is preferably formed from a titanium or an alloy thereof.

Fixator 28 is versatile and provides strong, stable support for fixing and compressing bone fractures. Barrel 46 of fixator 28 provides increased strength for fixing and compressing main bone fragments. Because support portion 50 extends partially about barrel 46 and provides additional buttressing area in contact with femur 24, support portion 50 better stabilizes head 44 of fixator 28 on the surface of condyles 26 of femur 24. In addition, support portion 50 adds versatility to the use of fixator 28. Because support portion 50 of head 44 provides a buttressing surface for supporting supplemental lag screws 38, fixator 28 is also capable of fixing and compressing smaller bone fragments caused by comminuted fractures. Fixator 28 may be used to solely fix and compress main bone fragments caused by a vertical fracture line. If necessary, fixator 28 may also be utilized to fix and compress additional smaller bone fragments by using supplemental lag screws 38.

Figure 2:
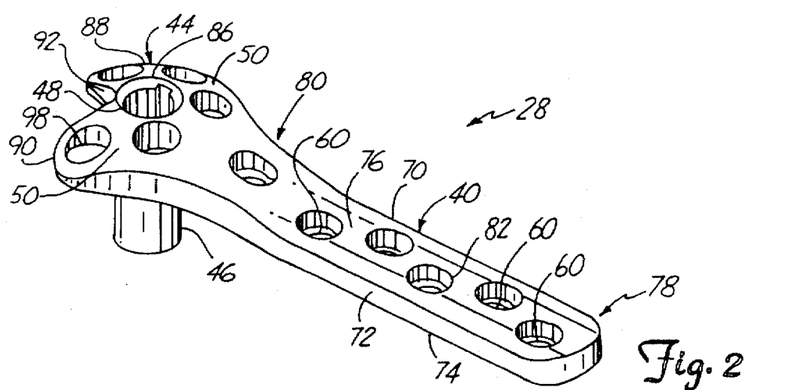
FIG. 2 is a perspective view of a fixator of the internal fixating system of FIG. 1.
Figure 3:
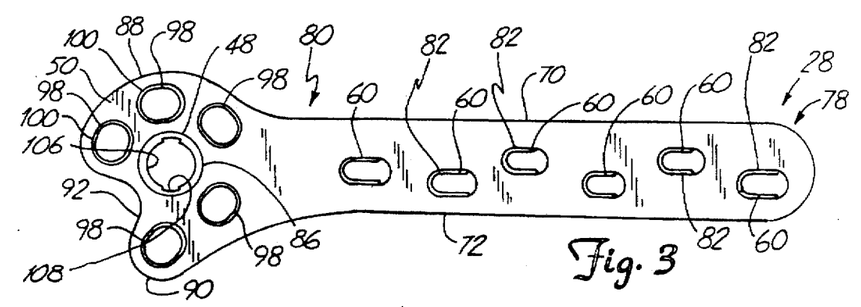
FIG. 3 is a top plan view of the fixator.
Figure 4:
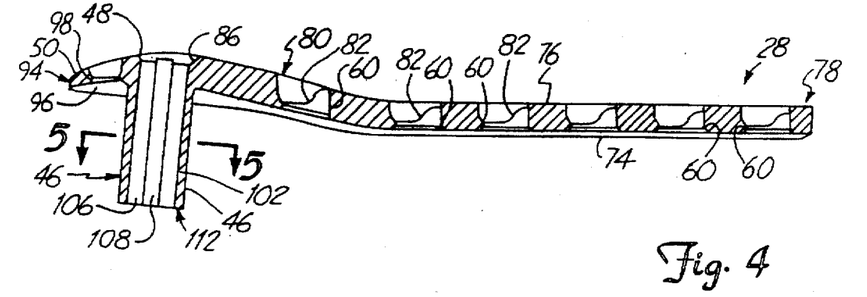
FIG. 4 is a cross-sectional view of the fixator.

FIGS. 2–4 illustrate fixator 28 of FIG. 1 in greater detail. FIG. 2 is a perspective view of fixator 28. FIG. 3 is a top plan view of fixator 28. FIG. 4 is a cross-sectional view of fixator 28. As best shown by FIGS. 2–4, plate portion 40 of fixator 28 is a generally elongated member defining apertures 60 and having a first side 70, a second side 72, a bottom surface 74, a top surface 76, a proximal end 78 and a distal end 80. The bottom surface 74 of plate portion 40 is preferably contoured so as to abut and conform with the curved surface of femur 24 (shown in FIG. 1). Preferably, bottom surface 74 is concave along a line parallel to a length of plate portion 40. Top surface 76 is preferably flattened along its length to provide a flatter, lower profile when implanted adjacent the surface of femur 24. Apertures 60 extend through plate portion between bottom surface 74 and top surface 76 and are sized for receiving bone screws 30 (shown in FIG. 1) so that fixator 28 may be secured to shaft portion 25 of femur 24. Apertures 60 are preferably provided with counter sunk holes 82 sized for receiving heads of bone screws 30. As a result, the contour of fixator 28 along top surface 76 has a low, smooth profile.

Distal end 80 of plate portion 40 preferably extends towards top surface 76 at an angle of about 164° with respect to the plane of the proximal end of plate portion. As a result, head 44 is raised with respect to plate portion 40 and conforms better to the shape of the distal end 22 of femur 24 and condyles 26 (shown in FIG. 1).

Head 44 integrally extends from distal end 80 of plate portion 40. Alternatively, head may be fixed or slidably coupled to plate portion 40 for modular assembly and adjustment of the length of fixator 28. As best shown by FIGS. 2–4, barrel portion 48 of head 44 comprises a portion of head 44 immediately surrounding and circumjacent to barrel 46. Barrel portion 48 is preferably centrally located along an axial center line of plate portion 40. Barrel portion 48 defines a central bore 86 in communication with barrel 46. As can be appreciated, barrel portion 48 may alternatively be off-set with respect to the axial center line of plate portion 40 and the center of head 44.

Support portion 50 comprises the portion of head 44 extending from barrel portion 48 away from plate portion 40. In particular, support portion 50 extends beyond both first and second sides 70 and 72 of plate portion 40 and distally away from distal end 80 of plate portion 40. Support portion 50 is preferably in the shape of a baseball catcher's mitt and includes circular portion 88 and thumb portion 90. Circular portion 88 extends away from first side 70 of plate portion 40 and preferably has a radius greater than one-half of a width of plate portion 40 between first side 70 and second side 72. Circular portion 88 preferably extends from first side 70 of plate portion 40 to a location between about 135°, and 180° from the axial center line of plate portion 40. Thumb portion 90 of the "catcher's mitt" configuration extends from barrel portion 48 away from second side 72 of plate portion 40. Preferably, thumb portion 90 extends from second side 72 of plate portion 40 in a direction between about 130° and 150° from a axial center line of plate portion 40. Circular portion 88 and thumb portion 90 are separated by a notch or gap 92 formed on a distal end 94 of head 44 opposite plate portion 40. Gap 92 is preferably positioned and sized to accommodate a popliteus muscle or cruciate ligament of the knee joint. Circular portion 88 and thumb portion 90 of support portion 50 define a plurality of apertures 98 for receiving supplemental lag screws 38 (shown in FIG. 1).

Apertures 98 extend through support portion 50 and preferably include counter-sunk holes 100 for receiving heads of supplemental lag screws 38. Apertures 98 are preferably positioned circumjacent barrel portion 48, central bore 86 and barrel 46. Because apertures are circumferentially positioned about bore 86 of head 44 and barrel 46, stress from lag screws 38 is evenly distributed about barrel 46 and head 44. Because circular portion 88 and thumb portion 90 of support portion 50 provide locations for supporting a plurality of lag screws 38 about barrel 46, multiple smaller bone fractures may be fixed and compressed by supplemental lag screws 38 in conjunction with the stronger compression of a vertical fracture line provided by barrel 46. As best shown by FIG. 4, support portion 50 of head 44 preferably has a concave bottom surface 96 for abutting a surface of the condyle. As a result, support portion 50 better stabilizes head 44 of fixator 28 for more secure positioning of fixator 28 against the bone and for more secure positioning of supplemental lag screws 38 (shown in FIG. 1) in the fractured bone. As can be appreciated, support portion 50 of head may have any one of a variety of shapes and configurations. For example, support portion may alternatively comprise a single arm or a plurality of arms or fingers projecting from central portion 50 in any one of various directions away from barrel portion 48 and plate portion 40.

Figure 5:
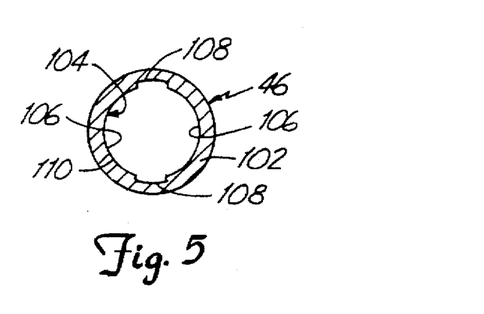
FIG. 5 is a cross-sectional view of the fixator taken along line 5—5 of FIG. 4.

FIG. 5 is a cross-sectional view of barrel 46 taken along line 5—5 of FIG. 4. As best shown by FIG. 5, barrel 46 is generally tubular in shape and includes a wall 102 which defines a generally cylindrical inner surface 104 and which has a substantially annular cross-section. Inner surface 104 includes arcuate portions 106 and detents 108. Arcuate portions 106 of inner surface 104 extend between detents 108 and partially define a generally circular bore 110 through barrel 46 for the reception of a lag screw. Bore 110 of barrel 46 is in communication with central bore 86 of head 44. Arcuate portions 106 of surface 104 are concentrically spaced from a center of bore 110 so as to have an inner diameter in close tolerance with an outer diameter of the lag screw received within bore 110. Arcuate portions 106 of surface 104 engage the lag screw to concentrically center the lag screw within bore 110 for guiding the lag screw within barrel 46 and for preventing substantial radial movement of the lag screw within barrel 46.

Detents 108 are formed along inner surface 104 between arcuate portions 106. Detents 108 generally comprise depressions or notches extending from arcuate portion 106 of surface 104 outward into wall 102 away from the center of bore 110. Detents 108 extend from a lower end 112 of barrel 46 towards head 44 along the entire length of barrel 46. Each detent 108 defines an elongated keyway along inner surface 104 of barrel 46. Detents 108 are shaped, sized and radially located for receiving keys or lugs on lag screws 32. Each detent 108 receives a key or lug projecting from a lag screw when the lag screw is inserted into bore 110 through end 112 so that barrel 46 and the particular lag screw may engage one another in a slidable yet non-rotatable fashion to prevent rotation of the lag screw and its coupled bone fragments with respect to barrel 46 and fixator 28. In the preferred embodiment illustrated, barrel 46 includes two opposite detents 108 extending into wall 102 for receiving a pair of opposite keys or lugs on a lag screw. As can be appreciated, depending upon the lag screw configuration, barrel 46 may alternatively have one or several detents 108 formed within wall 102.

Because detents 108 extend into wall 102 of barrel 46, detents 108 do not obtrude into the generally circular cross-section of bore 110 substantially defined by arcuate portions 106. As a result, bore 110 is also capable of receiving smooth, cylindrical keyless ends of non-keyed lag screws. Thus, barrel 46 of fixator 28 is usable with both keyed and keyless lag screws. Barrel 46 of fixator 28 provides an orthopedic surgeon flexibility in the selection of keyed and non-keyed barrel-lag screw configurations. Consequently barrel 46 of fixator 28 enables a single inventory of versatile fixators 28 to be maintained regardless of whether keyed or keyless lag screws are selected for fixing a bone fragment.

Figures 6, 7:
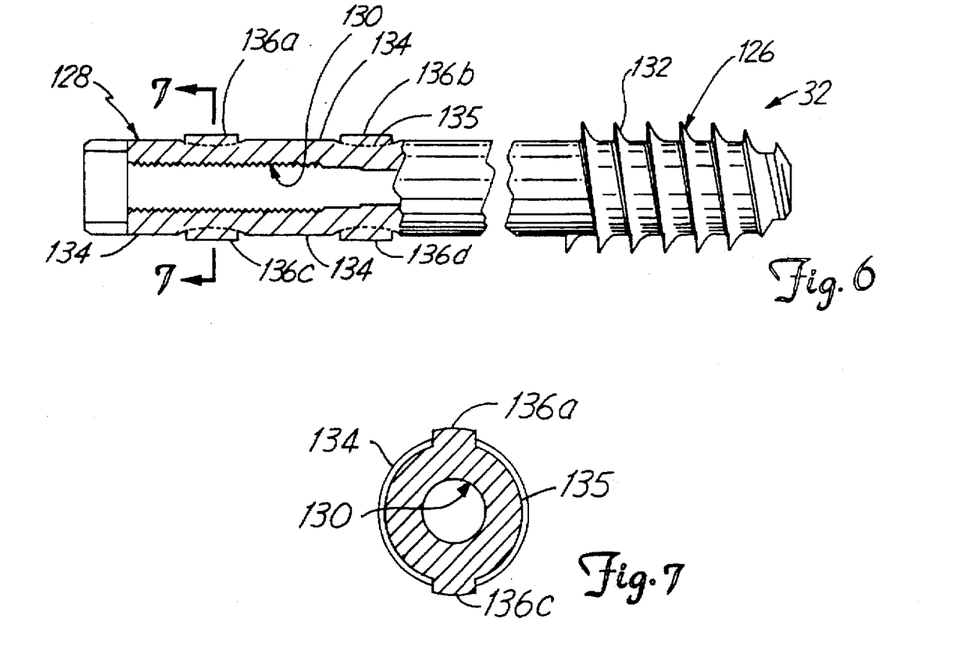
FIG. 6 is a fragmentary cross-sectional view of a keyed lag screw of the internal fixating system of FIG. 1.
FIG. 7 is a cross-sectional view of the keyed lag screw taken along line 7—7 of FIG. 6.
Figure 8:
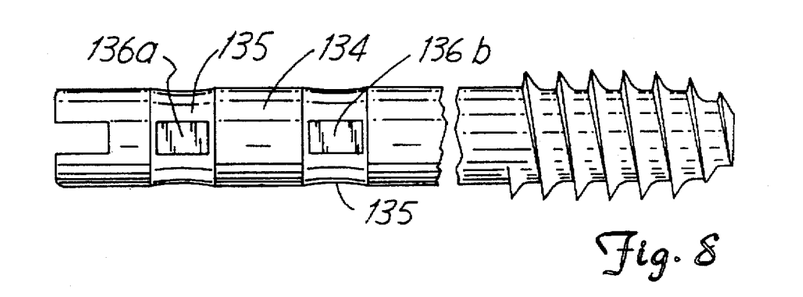
FIG. 8 is a top plan view of the keyed lag screw.

FIGS. 6–8 illustrate keyed lag screw 32 in greater detail. FIG. 6 is a fragmentary cross-sectional view of keyed lag screw 32. FIG. 7 is a cross-sectional view of keyed lag screw 32 taken along line 7—7 of FIG. 6. FIG. 8 is a top plane view of keyed lag screw 32. As discussed above, barrel 46 of fixator 28 (shown in FIGS. 2–5) is capable of slidably receiving keyed lag screw 32. As shown by FIG. 6, keyed lag screw 32 includes threaded end 126, keyed end 128 and bore 130. Threaded end 126 includes threads 132 for being threaded into a main bone fragment for fixing and lagging the main bone fragment for compression.

Keyed end 128 extends from threaded end 126 and includes a generally smooth cylindrical outer surface 134, lugs or keys 136a–136d and depressions 135. Cylindrical outer surface 134 circumferentially extends around keyed end 128 axially between keys 136a, 136c and keys 136b, 136d, axially between keys 136b, 136d and threaded end 126, and axially between keys 136a, 136c and an end of keyed end 128. Outer surface 134 has a diameter equal or slightly less than the diameter of arcuate portions 106 of barrel 46 (shown in FIG. 5). Outer surface 134 engages arcuate portions 106 to rigidly secure keyed lag screw 32 within barrel 46.

Depressions 135 circumferentially extend around keyed end 128 circumferentially between keys 136a–136d. Depressions 135 preferably have a maximum depth of about 0.003 inches and an axial length slightly larger than the axial length of keys 136. Depressions 135 reduce friction between keyed end 128 of shaft 32 and barrel 46 of fixator 28. As a result, lag screw 32 is more easily inserted into barrel 46 and more easily retracted during compression of the main bone fragments.

Keys 136a–136d extend outward away from an axial center line of lag screw 32. Keys 136a–136d have a height equal to or less than the depth of detents 108 of barrel 46 (shown in FIG. 5). Keys 136a–136d have a minimum height above surface 134 sufficient to enable keys 136a–136d to adequately engage wall 102 of barrel 46 (shown in FIG. 5) to prevent rotation of lag screw 32. In the preferred embodiment, keys 136a–136d have a height of about 0.014 inches from the floor of depression 135. Each key 136a–136d preferably has an axial length of about 0.2 inches and a circumferential length of about 0.12 inches. Keys 136a and 136b and keys 136c and 136d are in axial alignment. Keys 136a and 136c and keys 136b and 136d are in circumferential alignment. Because lag screw 32 includes a pair of keys (keys 136a and 136c or keys 136b and 136d) positioned circumferentially opposite one another, keys 136 are less likely to slip out of detents 108 due to manufacturing tolerances. Keys 136a and 136b are preferably axially spaced from one another. Similarly, keys 136c and 136d are also axially spaced from one another. As a result, at least one key 136 is always aligned within a keyway formed by detents 108 so that keys 136 prevent accidental rotation of lag screw 32. In addition, because keys 136a–136d are axially spaced from one another keys 136a–136d have less surface area in contact with barrel 46. As a result, keys 136a–136d produce less friction and are more easily moved axially within barrel 46 during insertion and compression. In addition, keys 136a–136d require less material and have a lower weight once implanted across the fractured femur. As can be appreciated depending upon the number and circumferential positions of detents 108 in barrel 46, keys 136 may have a variety of circumferential and axial configurations. For example, keys 136 may alternatively extend along the entire axial length of keyed end 128 and may also alternatively comprise any of a number of circumferentially spaced lugs or keys 136.

Bore 130 extends from an end opposite threaded end 126 axially into and along an axial center line of lag screw 32. Bore 130 is internally threaded and sized for the reception of a compression screw. Inner bore 130 receives a compression screw so that rotation of the compression screw causes keyed lag screw 32 to retract such that threads 132 engage the bone fragment to retract the bone fragment for compression.

Figure 9:
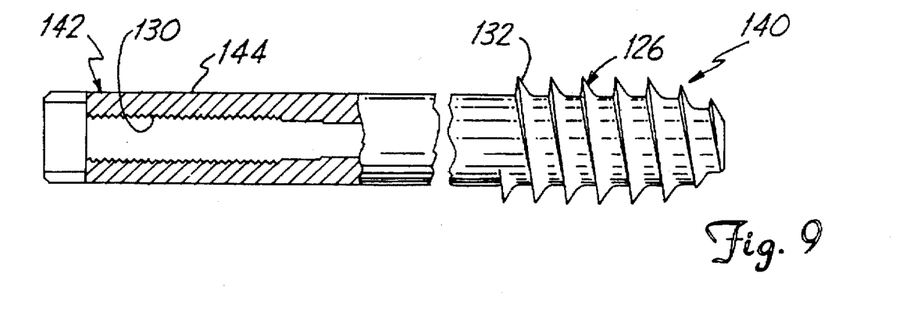
FIG. 9 is a fragmentary cross-sectional view of a keyless lag screw.

FIG. 9 illustrates a keyless lag screw 140 for use with fixator 28 of fixating system 20. FIG. 9 is a fragmentary cross-sectional view of keyless lag screw 140. For ease of illustration, those elements of keyless lag screw 140 which are the same as those elements of keyed lag screw 32 are numbered similarly. Keyless lag screw 140 is identical to keyed lag screw 32 except that keyed end 128 of keyed lag screw 32 is replaced with keyless end 142. Keyless end 142 extends from threaded end 126 and forms a generally smooth cylindrical outer surface 144. Surface 144 has an outer diameter similar to surface 134 of keyed lag screw 32. Surface 144 preferably has an outer diameter less than or equal to arcuate surface 106. In contrast to keyed end 128 of keyed lag screw 32, keyless end 142 of keyless lag screw 140 does not include keys. As a result, keyless lag screw 140 is rotatable within barrel 46 (shown in FIG. 5). In addition, keyless lag screw 140 is easier to align with fixator 28 (shown in FIGS. 2–5) and is easier implant within the fractured femur. Because surface 144 of keyless lag screw 140 has an outer diameter substantially equal to that of surface 134 of keyed lag screw 32, both keyed lag screw 32 and keyless lag screw 140 are insertable within bore 110 of barrel 46. As a result, both lag screws 32 and 140 are usable with fixator 128 to provide greater versatility and flexibility in the selection of either keyed or keyless configurations.

Figure 10:
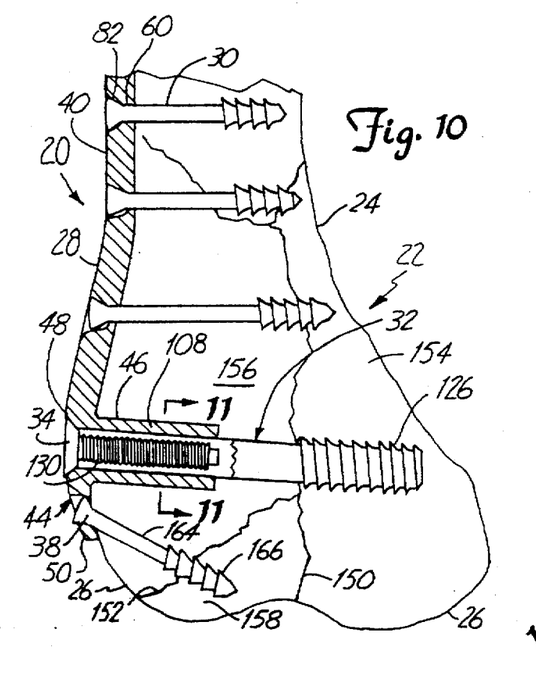
FIG. 10 is a cross-sectional view of the internal fixating system mounted to a distal end of a femur.
Figure 11:
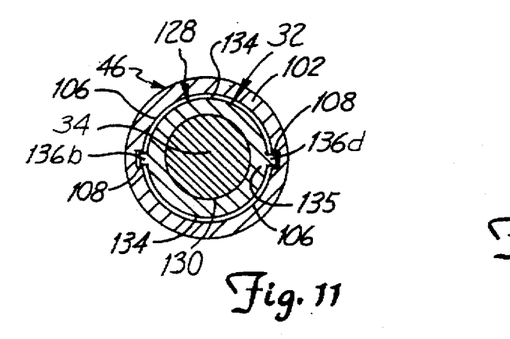
FIG. 11 is a cross-sectional view of the internal fixating system taken along line 11—11 of FIG. 10.

FIGS. 10 and 11 illustrate keyed lag screw 32 inserted within femur 24 and within barrel 46 of fixator 28. FIG. 10 is a fragmentary cross-sectional view of fixating apparatus 20 assembled and mounted adjacent to distal end 22 of femur 24. FIG. 11 is a cross-sectional view of barrel 46 and lag screw 32 taken along line 11—11 of FIG. 10. As best shown by FIG. 10, femur 24 is fractured about a vertical fracture line 1 50 and a comminuted fracture line 152 so as to form main bone fragments 154 and 156 and a smaller bone fragment 158. Keyed lag screw 32 and supplemental lag screws 38 fix and compress bone fragments 154, 156 and 158. In particular, threads 132 of threaded portion 126 of lag screw 32 extend into main bone fragment 154.

As best shown by FIG. 11, barrel 46 of fixator 28 slidably receives keyed end 128 of lag screw 32 in the axial direction (left-to-right as shown in FIG. 10). In particular, detents 108 slidably receive keys 136 of lag screw 32 to prevent rotation of lag screw 32 and main bone fragment 154 with respect to barrel 46 and main bone fragment 156. Arcuate portions 106 engage outer surface 134 of lag screw 32 to prevent inadvertent radial movement of lag screw 32 and main bone fragment 154 with respect to barrel 46 and main bone fragment 156. Arcuate portions 106 further guide axial movement of lag screw 32 during compression of lag screw 32. Overall, barrel 46 provides a strong and rigid support of lag screw 32 for better fixation and compression of main bone fragments 154 and 156. As can be appreciated, keyless lag screw 140 may be used in place of keyed lag screw 32.

As shown by FIG. 10, lag screw 32 is threadably fastened to condyle 26 of bone fragment 154. Barrel 46 of fixator 28 is assembled over lag screw 32. Compression screw 34 extends within and threadably engages threaded bore 130 of lag screw 32. Rotation of compression screw 34 retracts keyed end 128 of lag screw 32 within barrel 46 to retract threaded end 126 towards fixator 28. As a result, main bone fragment 154 is retracted and compressed against main bone fragment 156.

Supplemental lag screw 38 extends through support portion 50 circumjacent barrel 46 and barrel portion 48 of head 44. Supplemental lag screw includes a keyless end 164 and a threaded end 166. Threaded end 166 of supplemental lag screw 38 extends into bone fragment 158. Rotation of supplemental lag screw 38 causes bone fragment 158 to retract towards support portion 50 of head 44. Lag screw 38 further fixes bone fragment 158 in place.

Fixator 28 is mounted along a shaft portion 25 of femur 24 by bone screws 30. Because fixator 28 is configured for fixing bone fractures in the distal end 22 of femur 24 (knee fractures), barrel 46 extends from fixator 28 at between about 85° to about 100°. Preferably, barrel 46 extends from head 44 of fixator 28 at about 95° with respect to plate portion 40.

As discussed above, barrel 46 of fixator 28 is capable of receiving both keyed and keyless lag screws as shown in FIGS. 6 and 7. Thus, fixator 28 is versatile and reduces fixator inventories required for both keyed and keyless configurations. Barrel 46 and lag screw 32 provide a more rigid and strong compression and fixation of main bone fragments 154 and 156. In addition, because head 44 of fixator 28 includes support portion 50 extending from barrel portion 48 away from plate portion 40, head 44 additionally buttresses condyle 26 and supports supplemental lag screws 38 for fixing and compressing smaller bone fragments caused by comminuted fracture lines.

Figure 12:
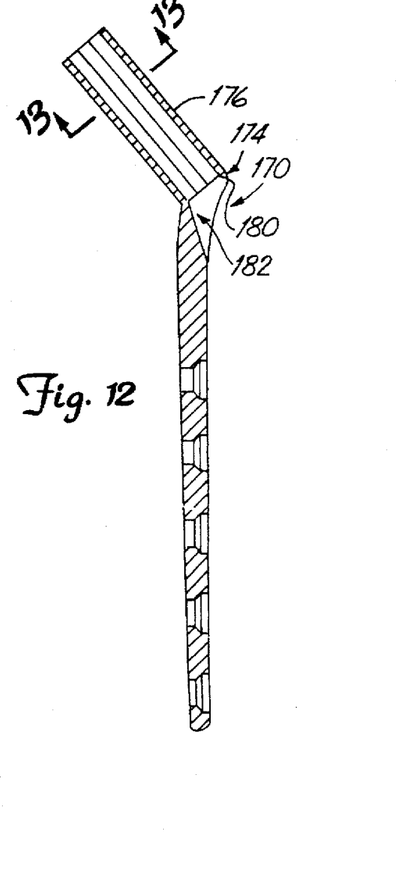
FIG. 12 is a cross-sectional view of an alternate embodiment of the fixator of FIGS. 2–5.
Figure 13:
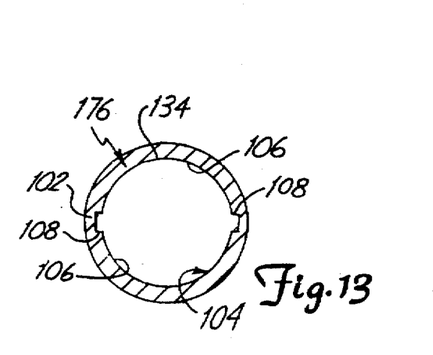
FIG. 13 is a cross-sectional view of the fixator taken along line 13—13 of FIG. 12.

FIGS. 12 and 13 illustrate an alternate embodiment (fixator 170) of fixator 28 shown in FIGS. 2-5. FIG. 12 is a cross sectional view of fixator 170. FIG. 13 is a cross-sectional view of fixator 170 taken along lines 13—13 of FIG. 12. For ease of illustration, those elements of fixator 170 which are the same as those elements of fixator 28 are numbered similarly. Fixator 170 is similar to fixator 28 except that head 44 and barrel 46 of fixator 28 are replaced with head 174 and barrel 176, respectively. Head 174 of fixator 170 includes a barrel portion 180 which defines a central bore 182. Barrel portion 180 supports barrel 176.

Barrel 176 preferably integrally extends from barrel portion 180 of head 174. Barrel 176 is similar to barrel 46 except that barrel 176 extends from head 174 at an angle of between about 130° to about 150° with respect to plate portion 40. Preferably, barrel 176 extends from head 174 at an angle of about 135° with respect to plate portion 40. As a result, barrel 176 is oriented at an angle for supporting a lag screw for fixing and compressing bone fractures in a proximal end of the femur (hip fractures). Similar to barrel 46 of fixator 28, barrel 176 of fixator 170 includes a wall 102 which defines generally cylindrical inner surface 104 having a substantially annular cross-section. Inner surface 104 includes arcuate portions 106 and detents 108. As discussed above, each detent 108 receives a key or lug projecting from a lag screw when the lag screw is inserted into bore 106 so that barrel 176 and the particular lag screw may engage one another in a slidable yet non-rotatable fashion to prevent rotation of the lag screw and its coupled bone fragments with respect to barrel 176 and fixator 170. Because detents 108 extend into wall 102 of barrel 176, detents 108 do not obtrude into the generally circular cross-section of bore 110 substantially defined by arcuate portions 106. As a result, bore 110 is also capable of receiving smooth, cylindrical keyless ends of non-keyed lag screws. Thus, barrel 176 of fixator 170 provides an orthopedic surgeon flexibility in the selection of keyed and non-keyed barrel-lag screw configurations. Barrel 176 of fixator 170 enables a single inventory of versatile fixators 170 to be maintained regardless of whether keyed or keyless lag screws are selected for fixing a bone fragment.

Figures 14, 15, 16:
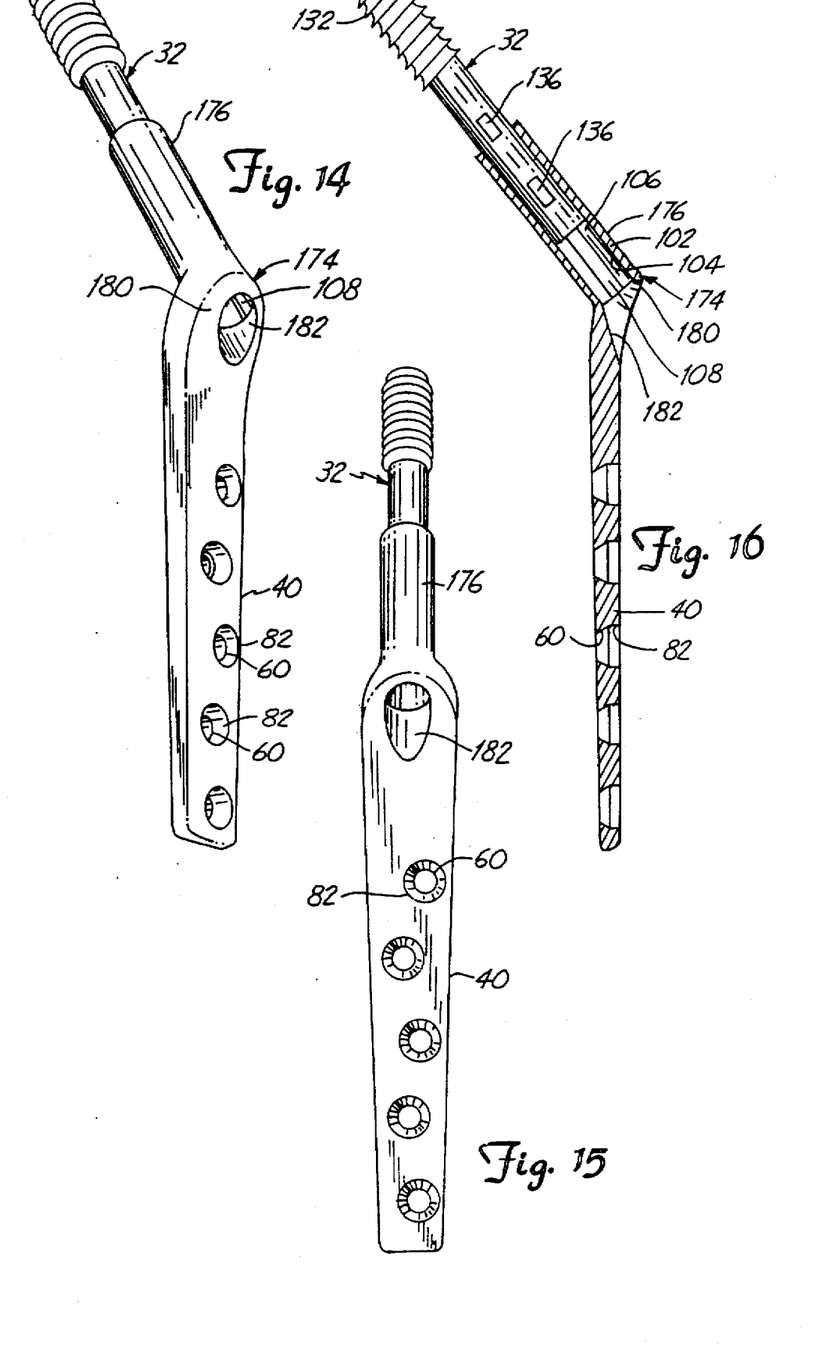
FIG. 14 is a perspective view of the keyed lag screw of FIGS. 6–8 coupled to the fixator of FIG. 12.
FIG. 15 is a top plan view of the lag screw and fixator of FIG. 14.
FIG. 16 is a partial cross-sectional view of the lag screw and fixator of FIG. 14.

FIGS. 14–16 illustrate keyed lag screw 32 inserted within barrel 176 of fixator 170. As shown by FIGS. 14–16, barrel 176 supports lag screw 32 at an angle of about 135° with respect to plate portion 40 for fixing and compressing bone fragments at a proximal end of the femur. Detents 108 prevent rotation of lag screw 32 with respect to barrel 176. Alternatively, fixator 170 may receive a keyless lag screw such as that illustrated in FIG. 9. Use of a keyless lag screw facilitates faster and easier placement of fixator 170 upon the lag screw and the femur.

Although the present invention has been described with reference to preferred embodiments, workers skilled in the art will recognize that changes may be made in form and detail without departing from the spirit and scope of the invention.

What is claimed is:

1. A fixating system for internally fixating bone fractures, the system comprising:
   a fixator including:
      a plate portion, the plate portion defining at least one plate aperture extending through the plate portion for receiving fastening means to fasten the fixator to a shaft of a bone;
      a head portion extending from the plate portion; and
      a barrel extending from the head portion, the barrel having a length and a means for receiving at least one of a keyless lag screw and a keyed lag screw, the means defining at least one key way recessed into a cylindrical inner surface of the barrel along at least a portion of a length of the barrel, and
   a first keyed lag screw having a threaded end portion for fastening to a bone fragment and a smooth end portion for being slidably received within the barrel, the smooth end portion having a length and an outer surface defining at least one key protruding from and integral and unitary with the outer surface and extending at least partially along the length for being received by the key way of the barrel to prevent rotation of the first lag screw within the barrel; and
   a compression screw adapted to be threadably fastened to the smooth end portion of the first lag screw and configured to bear against the head portion of the plate portion to hold the bone fragment in compression.

2. The system of claim 1 wherein the first lag screw includes:
   a plurality of spaced keys at least partially along the length of the second smooth end portion.

3. The system of claim 1 further including:
   a second lag screw having a threaded end portion and a smooth end portion, the smooth end portion of a second lag screw being rotatable within the barrel of the fixator.

4. The system of claim 1 wherein the inner surface of the barrel of the fixator defines two opposite key ways.

5. The system of claim 1 wherein the first lag screw includes:
   two keys oppositely oriented about outer surface of the smooth end portion of the first lag screw.

6. The system of claim 1 wherein the lag screw further includes:
   a threaded bore extending through the second smooth end portion, the threaded bore sized for receiving a compression screw.

7. The system of claim 6 wherein the outer surface of the smooth end portion of the first lag screw further includes a depression surrounding each key to reduce sliding friction between the inner surface of the barrel of the fixator and the outer surface of the smooth end portion of the first lag screw.

8. A lag screw for use with an internal bone fracture fixator having a barrel with a cylindrical inner surface along its length with a key way for slidably receiving the lag screw, the lag screw comprising:
   a threaded end portion: and
   a smooth end portion including means for being slidably received within the barrel of the fixator and having a length, the means including an outer surface defining at least one key protruding at least partially along the length and being unitary with the outer surface for being received by the key way of the barrel of the fixator, and defining a depression extending about a periphery of the outer surface and surrounding each key to reduce sliding friction between the outer surface of the smooth end portion of the lag screw and the barrel of the inner surface of the barrel of the fixator barrel.

9. A fixating kit for internally fixating bone fractures, the kit comprising:

a fixator including:
  a plate portion, the plate portion defining at least one plate aperture extending through the plate portion for receiving fastening means to fasten the fixator to a shaft of a bone;
  a head portion extending from the plate portion; and
  a barrel extending from the head portion, the barrel having a length and a means for receiving at least one of a keyless lag screw and a keyed lag screw, the means defining at least one key way recessed into a cylindrical inner surface of the barrel along at least a portion of the length of the barrel;

a first keyed lag screw having a threaded end portion for fastening to a bone fragment and a smooth end portion for being slidably received within the barrel, the smooth end portion having a length and an outer surface defining at least one key protruding outward from and integral and unitary with the outer surface and extending at least partially along the length for being received by the key way of the barrel to prevent rotation of the first lag screw within the barrel;

a second keyless lag screw having a threaded end portion for fastening to a bone fragment and a smooth end portion for being slidably received within the barrel, the smooth end portion of the second lag screw having a length and an outer surface adapted to be received by the barrel to permit rotation of the second lag screw relative to the barrel; and a compression screw adapted to be threadably fastened to the smooth end portion of one of the first lag screw and the second lag screw and configured to bear against the head portion of the plate portion to hold the bone fragment in compression, wherein one of the first lag screw and the second lag screw are inserted within the barrel of the fixator for use in fixating a bone fracture.

\* \* \* \* \*